United States Patent
Broad

(10) Patent No.: US 12,138,482 B2
(45) Date of Patent: Nov. 12, 2024

(54) MULTI-LEAF COLLIMATOR MODULE

(71) Applicant: Elekta Limited, Crawley (GB)

(72) Inventor: Martin Broad, Crawley (GB)

(73) Assignee: Elekta Limited, Crawley (GB)

( * ) Notice: Subject to any disclaimer, the term of this patent is extended or adjusted under 35 U.S.C. 154(b) by 237 days.

(21) Appl. No.: 17/906,147

(22) PCT Filed: Mar. 11, 2021

(86) PCT No.: PCT/EP2021/056270
§ 371 (c)(1),
(2) Date: Sep. 12, 2022

(87) PCT Pub. No.: WO2021/180898
PCT Pub. Date: Sep. 16, 2021

(65) Prior Publication Data
US 2023/0173304 A1   Jun. 8, 2023

(30) Foreign Application Priority Data

Mar. 13, 2020 (GB) ................................... 2003694

(51) Int. Cl.
*A61N 5/10* (2006.01)
(52) U.S. Cl.
CPC ......... *A61N 5/1045* (2013.01); *A61N 5/1048* (2013.01)
(58) Field of Classification Search
None
See application file for complete search history.

(56) References Cited

U.S. PATENT DOCUMENTS

| | | | |
|---|---|---|---|
| 6,459,769 B1 * | 10/2002 | Cosman | G21K 1/04 378/65 |
| 7,085,355 B1 | 8/2006 | Albagli et al. | |
| 7,167,542 B2 * | 1/2007 | Juschka | G21K 1/046 378/150 |

(Continued)

FOREIGN PATENT DOCUMENTS

| | | |
|---|---|---|
| CN | 201226257 Y | 4/2009 |
| CN | 202128818 U | 2/2012 |

(Continued)

OTHER PUBLICATIONS

"U.S. Appl. No. 17/906,149 Preliminary Amendment Filed with Application", 7 pgs.

(Continued)

*Primary Examiner* — Marcus H Taningco
(74) *Attorney, Agent, or Firm* — Schwegman Lundberg & Woessner, P.A.

(57) ABSTRACT

A multi-leaf collimator module for a radiotherapy device comprises: a leaf bank comprising a plurality of leaves. The module also comprises a leaf guide arranged to guide linear movement of the leaves in a first direction and a second direction opposite the first direction, the leaf guide being in direct contact with the leaves. The module further comprises a plurality of leaf actuators, each leaf actuator arranged to engender relative linear motion in the first direction and second direction between one leaf in the leaf bank and other leaves in the leaf bank; and a leaf bank actuator arranged to engender relative linear motion in the first direction and second direction between the entire leaf bank and the leaf guide.

20 Claims, 2 Drawing Sheets

(56) References Cited

U.S. PATENT DOCUMENTS

| | | | |
|---|---|---|---|
| 8,384,049 B1 | 2/2013 | Broad | |
| 8,718,234 B2* | 5/2014 | Echner | A61N 5/1045 378/152 |
| 2002/0101959 A1 | 8/2002 | Kato et al. | |
| 2006/0193441 A1* | 8/2006 | Cadman | A61N 5/1042 378/153 |
| 2009/0262901 A1 | 10/2009 | Broad et al. | |
| 2011/0026683 A1 | 2/2011 | Broad et al. | |
| 2011/0199085 A1 | 8/2011 | Allen et al. | |
| 2012/0076269 A1 | 3/2012 | Roberts | |
| 2017/0087386 A1 | 3/2017 | Mellenberg et al. | |
| 2017/0148536 A1 | 5/2017 | Kawrykow et al. | |
| 2018/0035969 A1 | 2/2018 | Jin | |
| 2018/0161602 A1 | 6/2018 | Kawrykow et al. | |
| 2020/0185119 A1* | 6/2020 | Stahl | G21K 1/046 |
| 2021/0290979 A1* | 9/2021 | Liu | A61N 5/1077 |

FOREIGN PATENT DOCUMENTS

| | | |
|---|---|---|
| CN | 204502129 U | 7/2015 |
| CN | 205460495 U | 8/2016 |
| CN | 205656865 U | 10/2016 |
| CN | 205843700 U | 12/2016 |
| CN | 107929955 A | 4/2018 |
| CN | 110538387 A | 12/2019 |
| DE | 3030332 A1 | 2/1982 |
| EP | 0314214 A2 | 5/1989 |
| EP | 3053628 A1 | 8/2016 |
| EP | 3266501 A1 | 1/2018 |
| GB | 2423909 | 9/2006 |
| JP | 2006081585 A | 3/2006 |
| JP | 2008206563 A | 9/2008 |
| WO | WO-2008076035 A1 | 6/2008 |

OTHER PUBLICATIONS

"U.S. Appl. No. 17/906,153 Preliminary Amendment Filed with Application", 8 pgs.
"International Application Serial No. PCT/EP2021/056276, International Search Report dated Jun. 17, 2021", (Jun. 17, 2021), 3 pgs.
"International Application Serial No. PCT/EP2021/056276, Written Opinion dated Jun. 17, 2021", (Jun. 17, 2021), 5 pgs.
"International Application Serial No. PCT/EP2021/056278, International Search Report dated Jun. 16, 2021", (Jun. 16, 2021), 3 pgs.
"International Application Serial No. PCT/EP2021/056278, Written Opinion dated Jun. 16, 2021", (Jun. 16, 2021), 6 pgs.
"International Application Serial No. PCT/EP2021/056281, International Search Report dated Jun. 16, 2021", (Jun. 16, 2021), 3 pgs.
"International Application Serial No. PCT/EP2021/056281, Written Opinion dated Jun. 16, 2021", (Jun. 16, 2021), 5 pgs.
"International Application Serial No. PCT/EP2021/056282, International Search Report dated Jun. 16, 2021", (Jun. 16, 2021), 3 pgs.
"International Application Serial No. PCT/EP2021/056282, Written Opinion dated Jun. 16, 2021", (Jun. 16, 2021), 5 pgs.
"United Kingdom Application Serial No. 2003664.6, Examination Report dated Aug. 13, 2020", (Aug. 13, 2020), 7 pgs.
"United Kingdom Application Serial No. 2003673.7, Examination Report dated Sep. 15, 2020", (Sep. 15, 2020), 6 pgs.
"United Kingdom Application Serial No. 2003679.4, Examination Report dated Sep. 15, 2020", (Sep. 15, 2020), 8 pgs.
"United Kingdom Application Serial No. 2003688.5, Examination Report dated Aug. 14, 2020", (Aug. 14, 2020), 6 pgs.
"International Application Serial No. PCT/EP2021/056270, International Search Report dated Jun. 17, 2021", (Jun. 17, 2021), 3 pgs.
"International Application Serial No. PCT/EP2021/056270, Written Opinion dated Jun. 17, 2021", (Jun. 17, 2021), 5 pgs.
"United Kingdom Application Serial No. 2003694.3, Combined Search and Examination Report mailed Sep. 15, 2020", 7 pgs.
"U.S. Appl. No. 17/906,149, Non Final Office Action mailed Jun. 18, 2024", 12 pages.
"U.S. Appl. No. 17/906,181, Non Final Office Action mailed Jul. 5, 2024", 9 pages.

* cited by examiner

MULTI-LEAF COLLIMATOR MODULE

PRIORITY APPLICATIONS

This application is a U.S. National Stage Filing under 35 U.S.C. § 371 from International Application No. PCT/EP2021/056270, filed on Mar. 11, 2021, and published as WO2021/180898 on Sep. 16, 2021, which claims the benefit of priority to United Kingdom Application No. 2003694.3, filed on Mar. 13, 2020; the benefit of priority of each of which is hereby claimed herein, and which applications and publication are hereby incorporated herein by reference in their entireties.

FIELD

The present disclosure relates to a multi-leaf collimator module for a radiotherapy device, and a multi-leaf collimator comprising the same.

BACKGROUND

Radiotherapeutic apparatus involves the production of a beam of ionising radiation, usually x-rays or a beam of electrons or other sub-atomic particles. This is directed towards a cancerous region of a patient, and adversely affects the tumour cells causing an alleviation of the patient's symptoms. The beam is delimited so that the radiation dose is maximised in the tumour cells and minimised in healthy cells of the patient, as this improves the efficiency of treatment and reduces the side effects suffered by a patient.

In a radiotherapy apparatus the beam can be delimited using a beam limiting device such as a 'multi-leaf collimator' (MLC). This is a collimator which consists of a large number of elongate thin leaves arranged side to side in an array. The leaves are usually made from a high atomic numbered material, usually tungsten, so that they are substantially opaque to the radiation.

Each leaf is moveable longitudinally so that its tip, or leading edge, can be extended into or withdrawn from the radiation beam. All the leaves can be withdrawn to allow the radiation beam to pass through, or all the leaves can be extended so as to block the radiation beam completely. Alternatively, some leaves can be withdrawn and some extended so as to define any desired shape, within operational limits. The array of leaf tips can thus be positioned so as to define a variable edge to the collimator. A multi-leaf collimator usually consists of two banks of such arrays (i.e. leaf banks), each leaf bank projecting into the radiation beam from opposite sides of the collimator. The variable edges provided by the two leaf banks thus collimate the radiation beam to a chosen cross-sectional shape, usually that of a target tumour volume to be irradiated. That is, the two leaf banks combine to provide an aperture of variable shape for shaping the radiation beam.

The movement of the leaf banks as a unit and the movement of the individual leaves may be carried out for different purposes. The movement of the individual leaves may be carried out to define the shape of the radiation beam, whereas the movement of the leaf banks may be carried out in order to move the shaped aperture provided by the leaves relative to the axis of the radiation beam. The movement of the leaf banks and individual leaves may be carried out independently of each other and the movements may be carried out sequentially or concurrently depending on the requirements of the application. This allows greater flexibility than allowing individual leaf motion alone.

However, the mechanism or structure for moving and guiding the leaves can lead to inaccuracies in the positioning of the leaves relative to the substrate and/or the radiation beam. In addition, misalignment of the leaf banks relative to each other can affect the ability of the leaves of one of the leaf banks to interdigitate with, or match the position of, the leaves of the other leaf bank.

Existing solutions to this problem include systems employing high-precision linear actuators to move the leaf banks and leaves. However, such systems are expensive and increase the volume and/or footprint of the multi-leaf collimator, which can limit its integrability in some radiotherapy devices.

It is desirable to provide a multi-leaf collimator which addresses the abovementioned problems.

SUMMARY

Aspects and features of the present invention are set out in the accompanying claims.

BRIEF DESCRIPTION OF THE DRAWINGS

Specific embodiments are described below by way of example only and with reference to the accompanying drawings in which.

DETAILED DESCRIPTION OF THE EMBODIMENTS

Overview

Figure 1:
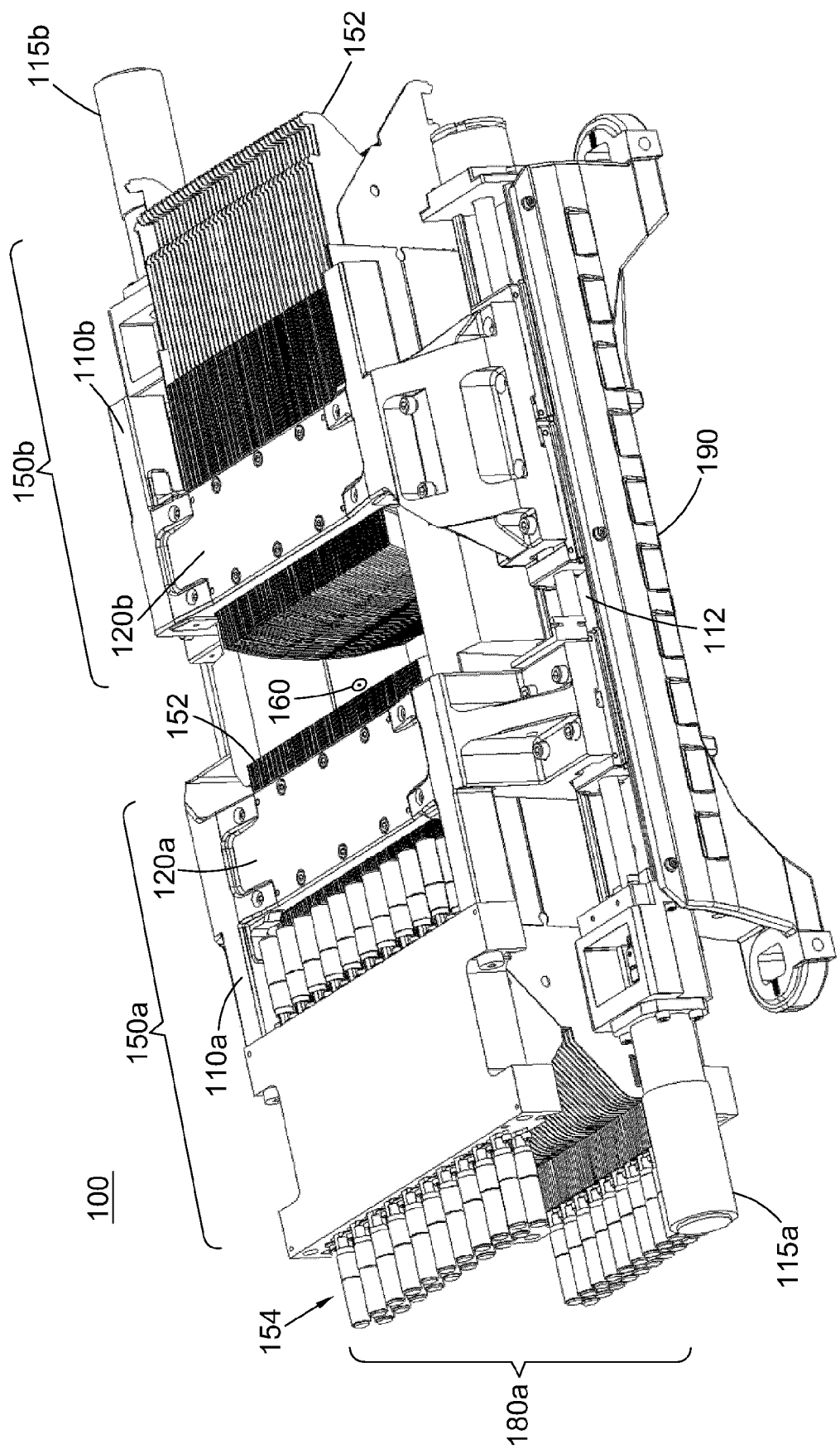
FIG. 1 shows a multi-leaf collimator according to the prior art.

In prior art MLCs, a leaf guide associated with each leaf bank performs two functions. First, the leaf guide acts as a guide for the movement of the individual leaves in the leaf bank when the leaves are moved relative to one another. The leaves engage with the leaf guide such that the lateral position of the tips of the individual leaves are governed by the leaf guide. Second, the leaf guide acts as an integral part of the carriage for moving the entire leaf bank (i.e. for moving all leaves in the leaf bank as a unit). That is, when the individual leaves of one leaf bank are moved relative to each other, the leaf guide associated with that leaf bank remains static relative to the moving leaves and therefore the leaves move relative to the leaf guide. A carriage, which moves linearly back and forth along a motor stage, carries the leaf bank. When the leaf bank is moved as unit, the leaf guide functions as part of the carriage, moving in unison with and carrying all leaves in the leaf bank.

The leaf guides move with the leaf banks. When moving the leaf banks there may be unintended lateral movement, for example due to manufacturing tolerances in the motor stages, translates into unintended lateral movement of the leaf guides, and therefore of the leaf tips, when the leaf bank is moved as unit.

This unintended lateral movement means the position of the leaves of the multi-leaf collimator relative to the other component of the radiotherapy device, in particular to the radiation beam, may not be accurately known or controlled. Additionally, as separate carriages carry the leaf banks in the multi-leaf collimator, the risk of lateral misalignment of the leaves of one leaf bank relative to the other leaf bank increases with decreasing tolerances in the stages on which the carriages move. Therefore, in prior art MLCs, accurate and reliable lateral positioning of the leaves along the full range of motion of the leaf banks is assured by the manufacturing tolerance/accuracy of the carriage stages. However, this increases the cost and complexity of the MLC.

In embodiments, a 'leaf bank actuator' replaces the carriage as the primary means for moving the leaf bank as whole. An important characteristic of the leaf bank actuator is that it moves the leaf bank as a unit relative to the leaf guide. The leaf bank actuator pushes the leaf bank back and forth relative to the leaf guide while the leaves are in contact with the leaf guide. This allows the leaf guide to guide the movement of the leaves both when the individual leaves are moved relative to each other and when the leaf bank is moved as a unit.

The leaf guide's guidance of the leaves when the leaf bank moves as one unit allows more accurate and reliable lateral positioning of the leaves along the full range of motion of the leaf bank. A further advantage is that the leaf guide can remain in a fixed position in the reference frame of the beam limiting device (or MLC) while the leaf bank moves in this frame of reference. With a static leaf guide, the lateral position of the leaves relative to the radiation beam can be more easily controlled along the full range of motion of the leaf bank. In addition, the lateral position of the leaves in one leaf bank relative to other components of the MLC can be more easily controlled along the full range of motion of the leaf bank. For example, if the leaf guides of the two opposing leaf banks in a multi-leaf collimator are both static while the leaf bank moves, there can be more reliable matching of the lateral positions of the leaves of the one leaf bank relative to the other. In this way, the interdigitation of the leaves in opposing leaf banks can be made more reliable using a less complex and/or less expensive apparatus compared with the carriage design of prior art MLCs.

Prior Art MLC with Carriages to Move the Leaf Banks

In a typical multi-leaf collimator, the leaves are individually motorised in order to allow them to be moved into and out of the path of the radiation beam along a first axis (which axis is in the plane of the leaf and parallel to the longitudinal dimension of the leaf). Each leaf bank is mounted in a structure which is moveable on a motorised stage. This structure is usually referred to as a "carriage". Thus, the leaves are supported on and movable relative to their respective carriage, and each carriage is mounted on and moveable along the first axis relative to a substrate, base or mount. The carriages include leaf guides, which are structured for supporting and guiding the leaves in their travel back and forth along the first axis.

FIG. 1 shows a multi-leaf collimator 100 according to the prior art. The multi-leaf collimator includes two leaf banks 150a, 150b, each leaf bank 150a, 150b including a plurality of leaves 152. The leaves 152 are individually moveable longitudinally within the leaf bank 150a, 150b so that they can project into and out of the path of a radiation beam passing through an aperture 160 between the two opposing leaf banks 150a, 150b. The leaves 152 are relatively thin so as to allow a high-resolution aperture shape to be obtained, but they are relatively deep in the direction of the axis of the radiation beam in order to render them sufficiently opaque at X-ray energies. The leaves 152 are relatively elongate (relatively long in the direction perpendicular to their thickness and depth) so as to allow them to adopt a wide range of positions.

The leaves are guided and supported by leaf guides 120a, 120b. The leaf guides 120a, 120b are structures which support the weight of the leaves 152 and guide them in their linear motion into and out of the path of the radiation beam. In the multi-leaf collimator shown in FIG. 1, the leaf guides 120a, 120b are parts of respective carriages 110a, 110b which carry the leaves 152.

For each leaf bank 150a, 150b, there is a leaf actuator array 180a (not shown for one of the leaf banks 150b). Each leaf actuator array 180a includes an array of leaf actuators 154. Each leaf actuator comprises an assembly including a leaf motor, leaf actuator screw and leaf nut. An output shaft of the leaf motor is connected to one end of the leaf actuator screw so that rotation of the output shaft translates directly into rotation of the leaf actuator screw. The leaf actuator screw is engaged with the thread of the leaf nut and the leaf nut is rigidly coupled to the leaf. Thus, rotation of the leaf actuator screw relative to the leaf causes relative linear motion between the leaf actuator screw and the leaf nut (and hence also the leaf).

Thus, each leaf actuator 154 is arranged to drive a respective leaf so that the leaves 152 can be moved in their respective leaf banks 150a, 150b independently of each other. That is, each leaf actuator 154 is arranged to engender relative linear motion between one leaf 152 and the other leaves in the leaf bank. A suitable controller will typically be provided (not shown), which is arranged to provide signals to the leaf actuators 154 in order to move the appropriate leaf or leaves 152 to provide the required shape or position of the aperture 160.

The multi-leaf collimator 100 includes a base 190 arranged to carry and support the weight of the other components in use. The carriages 110a, 110b are linearly moveable along carriage (motor) stages 112 relative to the base 190. Respective carriage actuators 115a, 115b (e.g. carriage motors) are arranged to engender relative linear motion between each carriage 110a, 110b and the base 190. As the leaf guides 120a, 120b are part of (or are rigidly fixed to) their respective carriages 110a, 110b, the leaf guides 120a, 120b move with their respective carriages.

The leaf bank motion is dependent upon the leaf guide motion due to the rigid coupling of the carriage 110a to both the leaf actuator array 180a and the leaf guide 120a. Each leaf actuator array 180a is rigidly coupled to a mount which is part of (or rigidly attached to) a respective carriage 110a, 110b. In addition, each leaf guide 120a, 120b is rigidly attached to the respective carriage 110a, 110b. Therefore, for each leaf bank 150a, 150b, the leaf actuator array 180a is rigidly coupled to the leaf guide 120a, 120b via a mount or a portion of the carriage 110a, 110b so that movement of the part of the leaf actuator array 180a mounted to the carriage 110a is not permitted relative to the leaf guide 120a. Though a part of the leaf actuator array 180a is rigidly coupled to the carriage, individual movement of the leaves relative to the carriage is of course permitted, because the leaf actuators have moving parts (i.e. the leaf motor, leaf actuator screw and leaf nut described above) which are arranged to engender relative motion between the individual leaves and the carriage.

The linear motion of the leaf banks 150a, 150b due to actuation by the carriage actuators 115a, 115b is in the same direction as that of the leaves 152 due to the leaf actuators 154. That is, the carriage actuators 115a, 115b are arranged to move the carriages 110a, 110b and hence the leaf banks 150a, 150b, back and forth along a first axis (i.e. in a first direction and a second direction opposite the first direction); and the leaf actuators 154 are arranged to move the leaves

152 back and forth along the same first axis. The first axis is parallel to the longitudinal direction from the tail to the tip of the leaves.

All leaves and carriages can be driven in unison or individually, a control system suitable for monitoring and controlling the position of the leaves and carriages ensures that collisions between leaves and/or between carriages are avoided.

The movement of the carriages and the movement of the individual leaves may be carried out for different purposes. The movement of the individual leaves may be carried out to define the shape of the radiation beam, whereas the movement of the carriages may be carried out in order to move the shaped aperture provided by the leaves relative to the axis of the radiation beam. The movement of the carriages and leaves may be carried out independently of each other and the movements may be carried out sequentially or concurrently depending on the requirements of the application. Multi-leaf collimators of these types allow greater flexibility than those allowing individual leaf motion alone.

The use of moving carriages to move the leaf banks has the potential to lead to inaccuracies in the positioning of the leaves relative to the substrate and/or the radiation beam. The reason for this is that the motion stages on which the carriages move can cause small lateral movement of the carriages (i.e. small movements normal to the plane of the leaves). As the leaf guides are rigidly coupled to the carriages, and the leaves themselves are held laterally by the leaf guides, the lateral movement of the carriages translates into lateral movement of the leaves themselves.

Conventionally, this potential problem is solved by using high tolerancing in the manufacture of the linear translation stage (or stages) on which the carriages travel. As a result of the high tolerancing, the two leaf banks are not misaligned relative to each other, and the ability of the leaves of one of the leaf banks to interdigitate with, or match the position of, the leaves of the other leaf bank is unaffected. However, the high tolerancing required increases the complexity and cost of manufacture of the MLC.

MLC with Leaf Bank Actuator and Static Leaf Guide

Multi-leaf collimators described herein may be arranged with the intention that when the leaf bank is moves as a unit, it is moved relative to the leaf guide. The leaf guide can then be permanently static relative to a beam limiting device in which the multi-leaf collimator is installed.

Figure 2:
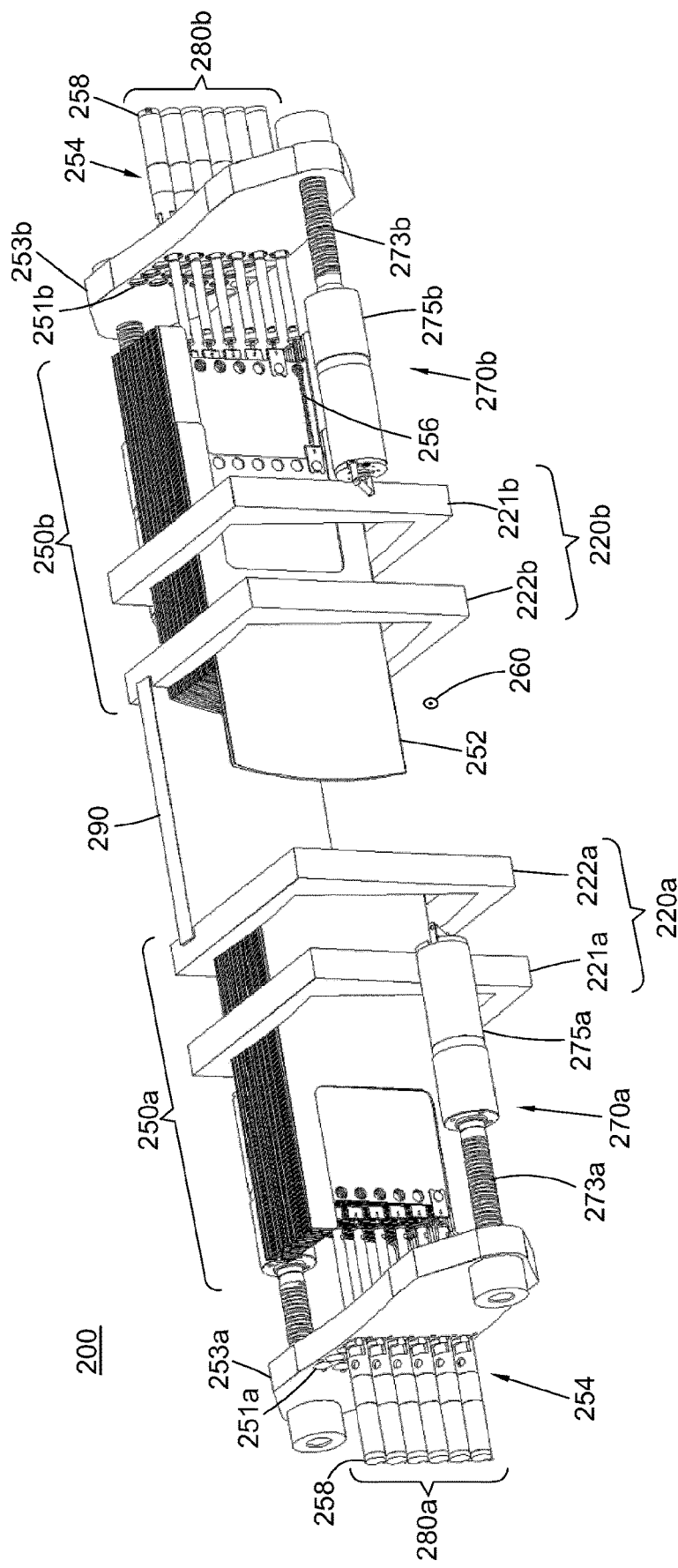
FIG. 2 shows a multi-leaf collimator according to an embodiment.

FIG. 2 shows a multi-leaf collimator 200 in accordance with an embodiment. The multi-leaf collimator 200 includes two leaf banks 250a, 250b, each leaf bank 250a, 250b including a plurality of leaves 252. The multi-leaf collimator 200 includes a leaf actuator array 280a, 280b for each leaf bank 250a, 250b. Each leaf actuator array 280a, 280b includes an array of leaf actuators 254. Each leaf actuator is arranged to engender linear motion of one leaf relative to the other leaves in the leaf bank. The arrays may be similar in form and function to the arrays of leaf actuators 154 shown in FIG. 1. Each leaf bank 250a, 250b is supported by a leaf guide 220a, 220b.

Leaves

The leaves of the multi-leaf collimator are the parts which define the shape of the aperture. The leaves are plate-like structures arranged side-by-side in a stack, much like playing cards in a deck of cards. The leaves can slide against each other and move independently of each other so that the 'deck' (i.e. the leaf bank) when viewed from the side has an outline at the ends which is defined by the position of the 'cards' (i.e. the leaves) relative to each other. Part of the radiation beam is blocked by the leaf bank so that the beam takes on a shape which is the same as the outline defined by the position of the leaves.

More particularly, the leaves 252 are each moveable longitudinally within their respective leaf bank 250a, 250b so that they can each project into and out of the path of a radiation beam passing through an aperture 260 between the two opposing leaf banks 250a, 250b. The leaves 252 may be described as plates. The leaves may be substantially rectilinear in shape in the plane thereof. The leaves 252 may be relatively thin in a direction perpendicular to both the direction of the axis of the beam and plane of the leaves, allowing a high-resolution aperture shape to be obtained. The leaves 252 may be relatively deep in the direction of the axis of the radiation beam in order to render them sufficiently opaque at X-ray wavelengths/energies. The leaves 252 may be relatively elongate (relatively long in the direction perpendicular to their thickness and depth), allowing them to adopt a wide range of positions while maintaining contact with the leaf guides. The leaves may comprise a dense material (high atomic number material), such as tungsten, which is capable of absorbing and/or scattering X-rays.

Leaf Guide

The leaf guide is the part of the multi-leaf collimator which prevents the leaves from moving except in the direction which allows them to move back and forth into and out of the path of the radiation beam. Much like the sleeve of a deck of playing cards, the leaf guides may be wrapped around the leaf bank so that the leaves are constrained so that they don't splay apart or fan out. The leaves may not actually contact each other and there may be a very small gap between each leaf. In this case, the leaves may be restrained laterally (i.e. prevented from splaying apart) by grooves in the leaf guides, each groove being arranged to receive a leaf and allowing the leaf to slide or run in the groove in its motion into and out of the path of the radiation beam.

More particularly, the leaves 252 are guided and supported by leaf guides 220a, 220b. The leaf guides 220a, 220b are structures which perform the functions of supporting the weight of the leaves 252 and/or guiding them in their linear motion into and out of the path of the radiation beam. The linear motion is back and forth along a single axis (i.e. the aforementioned first axis parallel to the plane of the leaves and perpendicular to the leading edges of the leaves). That is, each leaf guide 220a, 220b constrains movement of a respective leaf bank 250a, 250b to a single axis of movement. That is, each leaf guide 220a, 220b substantially prevents the movement of a respective leaf bank 250a, 250b along a second axis (that parallel to the propagation of the radiation beam when the multi-leaf collimator is in use; that is, the direction parallel to the leading edge of the leaves) and along a third axis (that substantially perpendicular to the plane of a leaf 252 in the leaf bank 250a, 250b). However, each leaf guide 220a, 220b allows linear movement of the respective leaf bank 250a, 250b and the individual leaves 252 of that leaf bank back and forth along the first axis.

The leaf guides 220a, 220b are differentiated from other components in that they perform said function(s) by being in direct contact with the leaves 252. Said direct contact may be described as dynamic contact in that the individual leaves 252 and the leaf bank 250a, 250b are moveable with respect to the leaf guide 220a, 220b.

Each leaf guide 220a, 220b may comprise a frame or support arranged to guide the leaf bank 250a, 250b and each of the individual leaves 252 in their linear motion. Each leaf guide 220a, 220b may comprise a frame having an opening through which the leaves are inserted. The opening may be rectilinear in shape to correspond to the cross-sectional shape of the leaf bank 250a, 250b, the cross section being taken in the plane perpendicular to the intended direction(s) of movement of the leaf bank into and out of the radiation beam (i.e. a plane parallel to that defined by the aforementioned second and third axes). Each leaf guide 220a, 220b may include grooves, protrusions or other features configured to engage with edges of the individual leaves of the leaf bank 250a, 250b to guide their movement through the leaf guide 220a, 220b and prevent their movement along the second and third axes.

In preferred embodiments, the leaf guides 220a, 220b each comprise a first leaf guide unit 221a, 221b and a second leaf guide unit 222a, 222b spaced from the first leaf guide unit along the first axis, wherein the first leaf guide unit 221a, 221b and second leaf guide unit 222a, 222b are each in direct contact with the respective leaf bank 250a, 250b. The leaf bank actuator 270a, 270b is arranged to engender relative linear motion between the leaf bank and both the first leaf guide unit 221a, 221b and the second leaf guide unit 222a, 222b. That is, the leaf bank actuator is arranged to engender relative linear motion between the leaf bank and the first leaf guide unit 221a, 221b, and to also engender relative linear motion between the leaf bank and the second leaf guide unit 222a, 222b. The first leaf guide unit 221a, 221b and the second leaf guide unit 222a, 222b may be rigidly coupled to one another, for example via the base 290 or via a coupling member.

Alternatively, the leaf guides 220a, 220b may each comprise only one leaf guide unit 221a, 221b in direct contact with the respective leaf bank 250a, 250b.

Advantageously, two or more spaced leaf guide units per leaf guide allow more accurate control of the positioning of the leaves and leaf banks compared with a single leaf guide unit. A longer single leaf guide unit spanning the same-sized portion of the leaves as the two leaf guide units may be used to achieve the same advantageous effect. However, this increases the weight of the multi-leaf collimator, which in turn affects the complexity and/or manoeuvrability of the beam limiting device within which it is installed.

Multi-Leaf Collimator Module

It may be understood that there is provided a module for a multi-leaf collimator comprising one half of the multi-leaf collimator shown in FIG. 2. That is, the module may comprise one leaf bank 250a, one leaf guide 220a, one array of leaf actuators 254, and one leaf bank actuator 270a arranged in any one or more of the configurations of one half of the multi-leaf collimator 200 described herein.

It may therefore be understood that there is provided a multi-leaf collimator module for a radiotherapy device, the module comprising a leaf bank supported by a leaf guide; and a leaf bank actuator arranged to engender relative linear motion between the entire leaf bank and the leaf guide.

There is also provided a multi-leaf collimator module for a radiotherapy device, the module comprising: a leaf bank comprising a plurality of leaves; a leaf guide arranged to guide linear movement of the leaves in a first direction and a second direction opposite the first direction, the leaf guide being in direct contact with the leaves; a plurality of leaf actuators, each leaf actuator arranged to engender relative linear motion in the first direction and second direction between one leaf in the leaf bank and other leaves in the leaf bank; and a leaf bank actuator arranged to engender relative linear motion in the first direction and second direction between the entire leaf bank and the leaf guide.

Such modules may be provided alone or provided connected to another similar module to form a dual-leaf-bank multi-leaf collimator such as the one shown in FIG. 2. The modules may each comprise a base 290, said bases having complementary inter-locating means for coupling the bases to each other. The interlocking means may comprise a groove, slot, recess, mortice or hole for receiving a suitably proportioned ridge, protrusion, tenon or stub. The inter-locating means may comprise interlocking means. The inter-locating means may be arranged to ensure relative alignment between the leaves of one of the modules with the leaves of the other module once the bases are located relative to each other using the inter-locating means.

Alternatively, the respective leaf guides 220a, 220b of the dual-leaf-bank multi-leaf collimator may be coupled to the same mounting structure. The mounting structure may be a base plate, frame or any other structure suitable to rigidly mount the leaf guides thereto. The mounting structure and (each) leaf guide may include a complementary pair of locating means for aligning (each) leaf guide 220a, 220b with the mounting structure. Such locating means may perform the function of allowing an accurate and reliable spatial relationship to be formed between each of the leaf guides 220a, 220b and the mounting structure when the leaf guides are coupled to the mounting structure.

Advantageously, the pair of locating means allows the leaf guide 220a, 220b (and hence the leaves 252 in the leaf bank 250a, 250b) to be more accurately and reliably aligned relative to the mounting structure. The locating means may comprise a male and female connector pair (for example, a protrusion and a hole, respectively) wherein one of the male and female connector is located on the mounting structure and the other one of the male and female connector is located on the respective leaf guide 220a, 220b. Alternatively, the locating means may comprise two female connectors, one on the mounting structure and one on the leaf guide 220a, 220b, allowing relative alignment between the mounting structure and the leaf guide by a pin or other male connector located partly in the female connector on the mounting structure and partly in the female connector on the leaf guide 220a, 220b.

Alternatively, in use the leaf guides 220a, 220b are each rigidly fixed to a base (or mount or housing or frame) 290 and/or rigidly fixed to each other. It may therefore be understood that the leaf guides 220a, 220b may be arranged to be static relative the base 290 in all modes of operation of the multi-leaf collimator 200. The leaf guides 220a, 220b may therefore remain static not only when leaves 252 are individually moved by their respective leaf actuators 254, but also when each leaf bank 250a, 250b is moved by its respective leaf bank actuator 270a, 270b. This may be achieved by rigidly coupling or fixing the leaf guides 220a, 220b to the base 290 so that no movement between the base 290 and leaf guides 220a, 220b is allowed, or by machining the leaf guides 220a, 220b and the base 290 from a single piece of material to form an integral or monolithic structure.

That is, the leaf guide(s) of one leaf bank may be rigidly connected to the leaf guide(s) of the opposing leaf bank either directly or indirectly via the base or a coupling member. That is, in the reference frame of the MLC, the position of the leaf guide(s) of one leaf bank may be fixed relative to the position of the leaf guide(s) of the opposing leaf bank. Advantageously, this provides a more reliable, less complex means of ensuring lateral alignment of the leaves of one leaf bank with the leaves of the opposing leaf bank.

Alternatively, one of the leaf guides 220a may have a mounting structure integrally formed (e.g. monolithically) therewith, the mounting structure being arranged to receive the other leaf guide 220b as described above.

It may therefore be understood that there is provided a multi-leaf collimator comprising a mount, a first multi-leaf collimator module as described herein and a second multi-leaf collimator module as described herein, wherein the respective leaf guides of the first multi-leaf collimator module and second multi-leaf collimator module are fixed to or integral with the mount and the respective leaf banks are arranged to face each other to define an aperture therebetween. The term 'face each other' here may mean that the leading edges of the leaves of one leaf bank face the leading edges of the leaves of the other leaf bank, which leading edges lie perpendicular to the direction(s) of movement of the leaves in the leaf guide. The arrangement of the leaf banks relative to each other is such that the shape of the aperture between them may be modified by movement of the leaves relative to the leaf guides.

Advantageously, as the leaf guides are static relative to the base, their alignment relative to the base and/or to each other can be fixed during manufacture. This provides a reduction in complexity and cost of manufacture of the multi-leaf collimator. Furthermore, the risk of lateral misalignment of the leaves (i.e. misalignment of the leaves in the direction normal to the plane of the leaves) during manufacture and/or in use is significantly reduced. That is, there are advantages to combining a leaf bank actuator as herein described (i.e. one arranged to engender relative motion between the entire leaf bank and the leaf guide) with a leaf guide which is static relative to a base or substrate of the multi-leaf collimator. For example, this configuration minimises lateral movement of the leaves during motion of the leaf bank when the entire leaf bank is moved under the force of the leaf bank actuator. Therefore, reliable and predictable movement of the leaves relative to the radiation beam and the target tissue can be achieved at lower cost and with lower complexity than needed in the prior art MLCs, such as the type shown in FIG. 1.

Embodiments include a first multi-leaf collimator module as described herein and second multi-leaf collimator module as described herein, wherein the leaf guide of the first multi-leaf collimator module is rigidly coupled to the leaf guide of the second multi-leaf collimator module.

That is, embodiments include a first multi-leaf collimator module according as described herein and a second multi-leaf collimator module as described herein, wherein the leaf guide of the first multi-leaf collimator module is arranged to remain static in relation to the leaf guide of the second multi-leaf collimator module during operation of the respective leaf bank actuators.

In the above described embodiments, the relative lateral alignment of a first leaf in one of the leaf banks and a second leaf in the other (opposing) leaf bank can be fixed in the manufacturing process. No or negligible lateral misalignment may occur when those leaves are moved by either their respective leaf actuators or their respective leaf bank actuators. Thus, a more accurately shaped or positioned aperture can be obtained and the leaves of on leaf bank can more reliably interdigitate with the leaves of the opposing leaf bank regardless of the position of the leaf banks along their range of motion.

Leaf Actuator Array/Leaf Actuators

The leaf actuator array is the part of the multi-leaf collimator which causes the individual leaves to move relative to each other. The leaf actuator array includes a leaf actuator for each leaf, each leaf actuator being the part which is responsible for the movement of a respective one of the leaves relative to the other leaves. The group of leaf actuators which operate on all the leaves of one leaf bank can be collectively referred to as the leaf actuator array.

More particularly, for each leaf bank 250a, 250b, there is a leaf actuator array 280a, 280b. Each leaf actuator array 280a, 280b includes an array of leaf actuators 254 (each comprising e.g. an assembly including a leaf motor, leaf actuator screw and leaf nut). The leaf actuator arrays 280a, 280b are arranged to move the leaves 252 in their respective leaf banks 250a, 250b independently of each other and relative to their respective leaf guides 220a, 220b. That is, each of the leaf actuators 254 in the array may be arranged to engender relative linear motion between the leaf 252 to which they are connected and other leaves in the leaf bank 250a. Each of the leaf actuators 254 in the array may be arranged to engender relative linear motion between the leaf 252 to which they are connected and the leaf guide 220a.

The leaf actuators 254 may each comprise a linear electric actuator. The leaf actuators 254 may comprise an acme screw, ball screw or lead screw assembly. The leaves 252 themselves may be coupled as a load to the end of a threaded rod acting as a leaf actuator screw 256. A leaf actuator driving mechanism 258 (henceforth described as a leaf motor 258 for brevity) driving the leaf actuator screw may be a DC, DC servo, DC brushless, DC brushless servo, AC, AC servo, or stepper motor. The leaf motor 258 may be coupled to the leaf actuator screw 256 at an end opposite to the end of the leaf actuator screw coupled to the leaf.

In FIG. 2, each leaf actuator includes a leaf actuator screw 256 having one end rigidly coupled to the tail portion of a leaf 252 (i.e. so as to be prevented from rotating or moving in a linear fashion relative to the leaf) and another end engaged with an internally threaded tube (e.g. a nut) coupled to the leaf motor 258 and arranged to rotate under the driving force of the leaf motor 258. Rotation of the threaded tube by the leaf motor 258 relative to the leaf actuator screw 256 translates into relative linear movement between the threaded tube and the leaf actuator screw 256. The linear movement of the leaf actuator screw 256 translates into linear movement of the leaf 252 due to the nature of the coupling therebetween.

However, it is not essential that the leaf actuator has the above described configuration. In some embodiments, the leaf actuator includes a leaf actuator screw which is coupled to an output shaft of the motor (or alternatively is the output shaft of the leaf motor). Thus, the leaf actuator screw rotates under the driving force of the leaf motor. A leaf nut having an internally threaded portion is incorporated into, or is mounted or coupled to, the tail portion of the leaf. The leaf nut is rigidly coupled to the tail portion of a leaf (i.e. so as to be prevented from rotating or moving in a linear fashion relative to the leaf) and the internally threaded portion engages with the thread of the leaf actuator screw. Thus, the rotational motion of the leaf actuator screw relative to the leaf nut translates into relative linear motion between the leaf actuator screw and the leaf nut and hence also the leaf. That is, as the leaf actuator screw is rotated by the leaf motor, it drives the leaf nut, and hence the leaf, in the direction parallel to the leaf actuator screw and in the plane of the leaf (i.e. along the first axis into and out of the path of the radiation beam when in use).

A rear or tail edge of the leaf (that is an edge opposite the leading edge of the leaf) may have an inset area to accommodate the leaf motor. The leaf may have an elongate aperture running along a substantial portion of the length of the leaf. The elongate aperture may be accessible to the leaf actuator screw via an internally threaded section (or the aforementioned leaf nut) which engages with the leaf actuator screw.

The stroke of the leaf actuator 254 may be sufficient to allow the leading edge of the leaf to be extended at least half way into the path of the radiation beam and also retract so that it is clear of the path of the radiation beam. The stroke may therefore be between about one half and about two times the diameter of the radiation beam for which the multi-leaf collimator is designed. The stroke may be between about one quarter the length of one leaf to about the length of one leaf Leaf Bank Actuator The leaf bank actuator is the part of the multi-leaf collimator which moves the whole of the leaf bank as a unit into and out of the path of the radiation beam. The leaf bank actuator moves the leaf bank in the same direction(s) as that in which the leaf actuator moves the leaves.

As described with reference to FIG. 1, the prior art multi-leaf collimators employ a leaf guide which moves together with the leaf bank actuator relative to the beam limiting device. That is, in the prior art, the leaf bank actuator (e.g. carriage) moves the leaf guide and the leaf bank together as one, whereas in the multi-leaf collimator of the type shown in FIG. 2, the leaf bank actuator moves the leaf bank relative to the leaf guide.

In embodiments, the leaf bank actuator moves the leaf bank relative to the leaf guide. In use, the leaf guide is static and the whole of the leaf bank moves back and forth through the leaf guide under the force applied by the leaf bank actuator.

More particularly, the multi-leaf collimator 200 shown in FIG. 2 includes a leaf bank actuator 270a, 270b for each leaf bank 250a, 250b. Generally, the leaf bank actuator in accordance with embodiments may be described as an actuator which is arranged to engender relative linear motion between the entire leaf bank and the leaf guide.

Each leaf bank actuator 270a, 270b may be coupled at a first end thereof to a respective leaf guide 220a, 220b or to the base 290, and at a second end thereof to the leaf bank 250a, 250b, for example via the leaf actuator array 280a, 280b. In use, the leaf bank actuator needs only a single anchor point at one end which is static, the other end of the actuator being coupled, directly or indirectly, to the leaf bank so that the leaf bank actuator can move the leaf bank relative to the static anchor point. The static anchor point may be static relative to the reference frame of a beam limiting device in which the multi-leaf collimator is installed. The static anchor point may be the leaf guide, the base or any other location on or in the beam limiting device which is, directly or indirectly, rigidly connected to the leaf guide.

A single leaf bank actuator may be provided for each leaf bank 250a, 250b. Each leaf bank actuator 270a, 270b is arranged to move its respective leaf bank 250a, 250b relative to the leaf guide 220a, 220b which supports that leaf bank 250a, 250b. That is, each leaf bank actuator 270a, 270b is arranged to engender relative linear motion between its respective leaf bank 250a, 250b and the leaf guide 220a, 220b supporting the leaf bank 250a, 250b.

The linear motion of the leaf banks 250a, 250b due to actuation by the leaf bank actuators 270a, 270b is in the same direction as that of the leaves 252 due to the leaf actuators 254. That is, the leaf bank actuators 270a, 270b are arranged to move the leaf banks 250a, 250b, in the aforementioned first direction and second direction; and the leaf actuators 254 are arranged to move the leaves 252 in the first direction and the second direction.

For each multi-leaf collimator module, the leaf bank actuator 270a, 270b may be coupled at a first node thereof to the leaf guide and at a second node thereof to the leaf bank 250a, 250b. The term node in this context means a location on the leaf bank actuator 270a, 270b suitable for fixture of other components thereto. The leaf bank actuator 270a, 270b is arranged to engender relative linear motion between the first node and the second node.

The first node may be located at a first end of the leaf bank actuator 270a, 270b and/or the second node may be located at a second end of the leaf bank actuator 270a, 270b opposite the first end. The first end and second end of the leaf bank actuator 270a, 270b may either refer to either absolute ends or end regions of the leaf bank actuator 270a, 270b. Advantageously, these locations of the first and second node allow the form and/or size of the multi-leaf collimator to be more compact and the size of a beam limiting device in which the multi-leaf collimator is installed may be reduced, or a form thereof improved. Hence, a size of a treatment head of the radiotherapy device in which the beam limiting device is installed may be reduced, of a form thereof improved.

The leaf bank actuator 270a, 270b may be coupled to the leaf bank 250a, 250b via the leaf actuator array 280a, 280b. The nature the coupling is such that the leaf actuators 254 may move leaves in the leaf bank 250a, 250b independently of each other relative to the leaf guide 220a, 220b, while the leaf bank actuators may move the leaves 252 in the leaf bank 250a, 250b in unison relative to the leaf guide 220a, 220b by moving the leaf actuators 254 relative to the leaf guide. The leaf bank actuator 270a, 270b may be coupled to the leaf motor, as opposed to the leaf actuator screw.

FIG. 2 shows leaf bank actuator plates 253a, 253b which can also be described as mounting plates for mounting the leaf actuators 254 thereto. Each of the leaf bank actuator plates 253a, 253b are positioned behind the trailing edges of the leaves 252 of their respective associated leaf bank 250a, 250b. The plane of the each of the leaf bank actuator plates 253a, 253b lies perpendicular to the aforementioned first and second directions. One face of each leaf bank actuator plates 253a, 253b faces in the first direction. That is, one face of each of the leaf bank actuator plates 253a, 253b faces the trailing edges of the leaves of its respective leaf bank 250a, 250b.

All leaf actuators 254 of a respective leaf bank 250a are coupled or mounted to the respective leaf bank actuator plate 253a. The leaf bank actuator plate 253a, 253b has a 2D array of through holes 251a, 251b therein. Each through hole 251a, 251b receives a leaf motor 258 therein so as to form a rigid coupling between the leaf motor 258 and the leaf bank actuator plate 253a, 253b. The coupling may be made rigid by the use of retainers, such as a screws or bolts (not shown), for fixing the leaf motors to the leaf bank actuator plate 253a, 253b.

The second end of each of the leaf bank actuators 270a, 270b (i.e. the end opposite the end coupled to the leaf guide 220a, 220b) is coupled to the respective leaf bank actuator plate 253a, 253b such that linear motion of the second end of the leaf bank actuator 270a. 270b in the first and second directions translates into linear motion of the leaf bank actuator plate 253a, 253b and hence the leaf motors 258 attached thereto, in the first and second directions. Thus, each leaf bank actuator 270a engenders relative linear motion between the leaf bank actuator plate 253a, 253b and the leaf guide 220a, 220b. Hence, the leaf bank actuator 270a engenders relative linear motion between all leaf motors 258 of the respective leaf bank 250a, 250b and the leaf guide 220a, 220b.

The leaf bank actuators 270a, 270b may each comprise a linear electric actuator. The leaf bank actuators 270a, 270b may comprise an acme screw, recirculating ball screw or lead screw assembly. The leaf banks 250a, 250b may be attached (optionally via the leaf actuator array 280a, 280b) as a load to the end of a threaded rod acting as a leaf bank actuator screw 273a, 273b. A leaf bank actuator driving mechanism (e.g. leaf bank actuator motor) 275a, 275b driving the leaf bank actuator screw 273a, 273b may be a DC, DC servo, DC brushless, DC brushless servo, AC, AC servo, or stepper motor. The leaf bank actuator motor 275a, 275b may be coupled to the leaf bank actuator screw 273a, 273b at an end of the leaf bank actuator screw opposite to that coupled to the leaf bank actuator plate 253a, 253b.

In FIG. 2, the leaf bank actuator screws 273a, 275b are coupled to an output shaft of the respective leaf bank actuator motor 275a, 275b (or alternatively are the output shafts of the leaf bank actuator motors). The leaf bank actuator motor 275a, 275b is rigidly coupled, directly or indirectly, to the leaf guide 220a, 220b. Thus, the leaf bank actuator screw 273a, 273b rotates under the driving force of the leaf bank actuator motor 275a, 275b. A leaf bank nut having an internally threaded portion is incorporated into, or is mounted or coupled to, the leaf bank actuator plate 253a, 253b. The leaf bank nut is rigidly coupled to the leaf bank actuator plate 253a, 253b (i.e. so as to be prevented from rotating or moving in a linear fashion relative to the leaf bank actuator plate) and the internally threaded portion thereof engages with the thread of the leaf bank actuator screw 273a, 273b. Thus, the rotational motion of the leaf bank actuator screw 273a, 273b relative to the leaf bank nut translates into relative linear motion between the leaf bank actuator screw 273a, 273b and the leaf bank nut and hence also the leaf bank actuator plate 253a, 253b. That is, as the leaf bank actuator screw 273a, 273b is rotated by the leaf bank actuator motor 275a, 275b, it drives the leaf bank nut, and hence the leaf, in the direction parallel to the axis of the leaf bank actuator screw 273a, 273b and in the plane of the leaf 252 (i.e. along the first axis into and out of the path of the radiation beam when in use).

However, it is not essential that the leaf bank actuator 270a, 270b has the above described configuration. In some embodiments, each leaf bank actuator 270a, 270b, includes a leaf bank actuator screw having one end rigidly coupled to a respective one of the leaf bank actuator plates 253a, 253b (i.e. so as to be prevented from rotating or moving in a linear fashion relative to the leaf bank actuator plate) and another end engaged with an internally threaded tube (e.g. a nut) coupled to the leaf bank actuator motor. The internally threaded tube is arranged to rotate under the power of the leaf bank actuator motor. Rotation of the threaded tube by the leaf bank actuator motor relative to the leaf bank actuator screw 273a, 273b translates into relative linear movement between the threaded tube and the leaf bank actuator screw.

The linear movement of the leaf bank actuator screw 273a, 273b translates into linear movement of the leaf bank actuator plate 253a, 253b due to the rigid coupling therebetween.

The stroke of the leaf bank actuator 270a, 270b may be sufficient to allow the leading edge of the leaves 252 to be extended at least half way into the path of the radiation beam and also retract so that it is clear of the path of the radiation beam. The stroke may therefore be between about one half and about two times the diameter of the radiation beam for which the multi-leaf collimator is designed. The stroke may be between about one quarter the length of one of the leaves and about twice the length of one of the leaves.

As shown in FIG. 2, a pair of leaf bank actuators may be provided per leaf bank. The pair may include one leaf bank actuator having a second end coupled to a first region of the leaf bank actuator plate 253a adjacent to a first edge, and another leaf bank actuator having a second end coupled to a second region of the leaf bank actuator plate 253a adjacent to a second edge. The second edge may be opposite to the first edge as shown in FIG. 2. However, embodiments are not limited to this arrangement and the pair of leaf bank actuators may be arranged in other configurations, such as near adjacent sides of the leaf bank actuator plates.

Advantageously, employing two leaf bank actuators per leaf bank provides improved stability and reliability/accuracy in leaf bank movement compared with only a single leaf bank actuator per leaf bank.

Control of the Actuators

A suitable controller will typically be provided (not shown), which is arranged to provide signals to the leaf actuators 254 and/or the leaf bank actuators 270a, 270b in order to move the appropriate leaf or leaves 252 to provide the required shape or position of the aperture 260. As the person skilled in the art will appreciate, the leaf actuators 254 and the leaf bank actuators 270a, 270b are connected to suitable drives for converting step, speed and/or direction input from the controller to actuator currents and voltages.

The leaf actuators control the motion of the leaves for the most granular delimitation, that is for controlling the shape of the edge of the aperture, whereas the leaf bank actuators control the motion of the entire leaf bank for the broader delimitation of controlling the overall position of the edge of the aperture. In the treatment environment, the requirements for the granular delimitation (aperture shape) are usually set by the shape of the target tissue (e.g. tumour) to be irradiated, whereas the requirements for the broader delimitation (aperture position) are usually set by the position of the target tissue to be irradiated. The target tissue may move during treatment due to movement of the patient, for example due to chest expansion and contraction during breathing. It is therefore important to accurately control the position of the aperture during treatment using the leaf bank actuators.

Advantageously, in contrast with the multi-leaf collimator shown in FIG. 1, the multi-leaf collimator according to embodiments has static leaf guides during movement of the entire leaf banks under the control of the leaf bank actuators. Therefore, a degree of movement of the leaf banks caused by movement of the leaf guides is eliminated and the position of the aperture is more accurately controlled.

The stability of the leaf guide provided by embodiments also has advantageous effects on the predictability and reliability of the position of individual leaves in the leaf banks. In the prior art multi-leaf collimators, the leaf guide moves with the leaf bank when the leaf bank actuator is in operation. This introduces the potential for disparities between predicted and actual leaf position owing to small, unwanted lateral displacements of the leaf guide, and hence leaves, during travel. In embodiments, since the leaf guide is static, such lateral displacements are minimised and thus the disparity between predicted and actual leaf position is minimised.

Therefore, in embodiments, the interrelationship between the leaf bank, the leaf bank actuator and the leaf guide provides a more predictable, accurate and reliable aperture shape and position. Thus, during treatment, the radiation dose provided to the target tissue can be maximised while the dose applied to healthy tissue surrounding the target tissue can be minimised.

There is presented a beam limiting device for limiting a beam of radiation, the beam limiting device comprising any of the multi-leaf collimators described herein. There is also presented a radiotherapy device comprising said beam limiting device.

There is also provided a method of driving any of the multi-leaf collimator modules described herein, the method comprising driving the leaf bank actuator to engender relative linear motion between the entire leaf bank and the leaf guide.

When the term, leaf bank actuator is used, this may be understood to mean a single actuator arranged to engender relative linear motion between the entire leaf bank and the leaf guide. The leaf actuator array cannot be considered to be a leaf bank actuator falling within this definition, because it contains multiple actuators which individually are incapable of moving the entire leaf bank relative to the leaf guide.

It may be understood that when the terms 'parallel', 'perpendicular' or 'in the plane of' are used to describe the relative arrangement of features and components, small deviations therefrom are permitted provided that they do not affect the functional and/or operational aspects of the multi-leaf collimator modules described herein.

Features of the above aspects can be combined in any suitable manner. It will be understood that the above description is of specific embodiments by way of aspect only and that many modifications and alterations will be within the skilled person's reach and are intended to be covered by the scope of the appendant claims.

The invention claimed is:

1. A multi-leaf collimator module for a radiotherapy device, the multi-leaf collimator module comprising:
   a leaf bank comprising a plurality of leaves;
   a leaf guide arranged to guide linear movement of the plurality of leaves in a first direction and a second direction opposite the first direction, the leaf guide being in direct contact with the plurality of leaves;
   a plurality of leaf actuators, wherein each leaf actuator arranged to cause relative linear motion in the first direction and second direction between a particular leaf in the leaf bank and one or more other leaves in the leaf bank; and
   a leaf bank actuator arranged to cause relative linear motion in the first direction and second direction between the entire leaf bank and the leaf guide.

2. The multi-leaf collimator module according to claim 1, wherein the leaf bank actuator is coupled at a first end thereof to the leaf guide and at a second end thereof to the leaf bank.

3. The multi-leaf collimator module according to claim 2, wherein the leaf bank actuator is coupled at the second end thereof to the leaf bank via one or more of the plurality of leaf actuators.

4. The multi-leaf collimator module according to claim 3, wherein each leaf actuator of the plurality of leaf actuators is coupled at a first end thereof to the second end of the leaf bank actuator and at a second end thereof to the particular leaf.

5. The multi-leaf collimator module according to claim 1, wherein each leaf actuator of the plurality of leaf actuators is coupled at a first end thereof to the leaf bank actuator and at a second end thereof to the particular leaf.

6. The multi-leaf collimator module according to claim 1, wherein the leaf bank actuator is arranged to cause relative linear motion between the entire leaf bank and the leaf guide by causing relative linear motion between the plurality of leaf actuators and the leaf guide.

7. The multi-leaf collimator module according to claim 1, wherein the leaf guide comprises:
   a first leaf guide unit; and
   a second leaf guide unit spaced from the first leaf guide unit in the first direction, wherein the first leaf guide unit and second leaf guide unit are in direct contact with the leaf bank.

8. A multi-leaf collimator comprising:
   a mount;
   a first multi-leaf collimator module; and
   a second multi-leaf collimator module, wherein each of the first multi-leaf collimator module and the second multi-leaf collimator module comprise:
      a leaf bank comprising a plurality of leaves;
      a leaf guide arranged to guide linear movement of the plurality of leaves in a first direction and a second direction opposite the first direction, the leaf guide being in direct contact with the plurality of leaves;
      a plurality of leaf actuators, wherein each leaf actuator arranged to cause relative linear motion in the first direction and second direction between a particular leaf in the leaf bank and one or more other leaves in the leaf bank; and
      a leaf bank actuator arranged to cause relative linear motion in the first direction and second direction between the entire leaf bank and the leaf guide;
   wherein the leaf guide of the first multi-leaf collimator module and the leaf guide of the second multi-leaf collimator module are fixed to or integral with the mount, and wherein a leading end of the leaf bank of the first multi-leaf collimator module and a leading end of the leaf bank of the second multi-leaf collimator module are arranged to face each other to define an aperture therebetween.

9. The multi-leaf collimator of claim 8, wherein the leaf guide of the first multi-leaf collimator module is rigidly coupled to the leaf guide of the second multi-leaf collimator module.

10. The multi-leaf collimator of claim 8, wherein the leaf guide of the first multi-leaf collimator module is arranged to remain static in relation to the leaf guide of the second multi-leaf collimator module during operation of at least one of the leaf bank actuator of the first multi-leaf collimator module or the leaf bank actuator of the second multi-leaf collimator module.

11. The multi-leaf collimator of claim 8, wherein the multi-leaf collimator is included on or coupled to a beam limiting device.

12. The multi-leaf collimator of claim 11, wherein the beam limiting device comprises:
   a controller arranged to drive at least one of the leaf bank actuator of the first multi-leaf collimator module or the leaf bank actuator of the second multi-leaf collimator module to cause relative linear motion between the leaf bank of the first multi-leaf collimator module and the leaf guide of the first multi-leaf collimator module or between the leaf bank of the second multi-leaf collimator module and the leaf guide of the second multi-leaf collimator module.

13. The multi-leaf collimator of claim 11, wherein the beam limiting device is included in or coupled to a radiotherapy device.

14. A method of driving a multi-leaf collimator module, the multi-leaf collimator module comprising:

a leaf bank comprising a plurality of leaves;

a leaf guide arranged to guide linear movement of the plurality of leaves in a first direction and a second direction opposite the first direction, the leaf guide being in direct contact with the plurality of leaves;

a plurality of leaf actuators, wherein each leaf actuator arranged to cause relative linear motion in the first direction and second direction between a particular leaf in the leaf bank and one or more other leaves in the leaf bank; and a leaf bank actuator arranged to cause relative linear motion in the first direction and second direction between the entire leaf bank and the leaf guide;

the method comprising:

driving the leaf bank actuator to cause relative linear motion between the entire leaf bank and the leaf guide.

15. The method of claim 14, wherein the leaf bank actuator is coupled at a first end thereof to the leaf guide and at a second end thereof to the leaf bank.

16. The method of claim 15, wherein the leaf bank actuator is coupled at the second end thereof to the leaf bank via one or more of the plurality of leaf actuators.

17. The method of claim 16, wherein each leaf actuator of the plurality of leaf actuators is coupled at a first end thereof to the second end of the leaf bank actuator and at a second end thereof to the particular leaf.

18. The method of claim 14, wherein each leaf actuator of the plurality of leaf actuators is coupled at a first end thereof to the leaf bank actuator and at a second end thereof to the particular leaf.

19. The method of claim 14, wherein the leaf bank actuator is arranged to cause relative linear motion between the entire leaf bank and the leaf guide by causing relative linear motion between the plurality of leaf actuators and the leaf guide.

20. The method of claim 14, wherein the leaf guide comprises:

a first leaf guide unit; and a second leaf guide unit spaced from the first leaf guide unit in the first direction, wherein the first leaf guide unit and second leaf guide unit are in direct contact with the leaf bank.

* * * * *